United States Patent
Baker et al.

(10) Patent No.: US 12,408,922 B2
(45) Date of Patent: Sep. 9, 2025

(54) PHARYNX ASPIRATION DEVICE FOR MINIMIZING INFECTIOUS PARTICLE EXPOSURE DURING ENDONASAL SURGERIES

(71) Applicant: Icahn School of Medicine at Mount Sinai, New York, NY (US)

(72) Inventors: Turner Baker, New York, NY (US); Alfred Marc Iloreta, New York, NY (US); Alexis Bruhat, New York, NY (US); Raj Shrivastava, New York, NY (US); Anthony Costa, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 263 days.

(21) Appl. No.: 18/009,621

(22) PCT Filed: Jun. 10, 2021

(86) PCT No.: PCT/US2021/036735
§ 371 (c)(1),
(2) Date: Dec. 9, 2022

(87) PCT Pub. No.: WO2021/252716
PCT Pub. Date: Dec. 16, 2021

(65) Prior Publication Data
US 2023/0218301 A1 Jul. 13, 2023

Related U.S. Application Data

(60) Provisional application No. 63/037,930, filed on Jun. 11, 2020.

(51) Int. Cl.
*A61B 17/12* (2006.01)
*A61B 17/24* (2006.01)

(52) U.S. Cl.
CPC .... *A61B 17/12104* (2013.01); *A61B 17/1204* (2013.01); *A61B 17/12136* (2013.01); *A61B 2017/246* (2013.01); *A61B 2217/005* (2013.01)

(58) Field of Classification Search
CPC ........ A61B 2217/005; A61B 17/12136; A61B 17/12104; A61B 17/24; A61B 17/1688;
(Continued)

(56) References Cited

U.S. PATENT DOCUMENTS

| | | | | |
|---|---|---|---|---|
| 5,372,131 | A * | 12/1994 | Heinen, Jr. | ........ A61M 16/0479 128/207.14 |
| 2003/0176886 | A1* | 9/2003 | Wholey | ............ A61M 25/0068 606/200 |

(Continued)

FOREIGN PATENT DOCUMENTS

WO WO-2018092150 A1 * 5/2018 ............ A61M 16/04

OTHER PUBLICATIONS

International Search Report and Written Opinion in PCT Application No. PCT/US2021/036735, mailed Oct. 13, 2021 (8 pages).
(Continued)

*Primary Examiner* — Katherine H Schwiker
*Assistant Examiner* — Lauren Dubose
(74) *Attorney, Agent, or Firm* — Leason Ellis LLP

(57) ABSTRACT

A method for minimizing infectious particle exposure during endonasal surgeries includes the steps of: introducing an aspiration device through a mouth of a patient and positioning a distal tip within the nasopharynx space, the aspiration device comprising an elongated balloon catheter having an inflatable balloon located within a distal region thereof and a distal aspiration port that is positioned distal to the balloon; inflating the balloon so that the balloon occupies the nasopharynx space; and aspirating any infectious particles within the nasopharynx space via the distal aspiration port.

13 Claims, 7 Drawing Sheets

(58) Field of Classification Search
CPC .......... A61B 17/3478; A61B 2017/246; A61B 1/233; A61M 2025/1086; A61M 2025/109; A61M 2025/1093; A61M 2025/0019; A61M 25/1002; A61M 25/007; A61M 25/10; A61M 25/0026; A61M 2210/0681; A61M 16/0434; A61M 16/0463
See application file for complete search history.

(56) References Cited

U.S. PATENT DOCUMENTS

| | | |
|---|---|---|
| 2005/0240147 A1 | 10/2005 | Makower et al. |
| 2006/0095066 A1* | 5/2006 | Chang .............. A61B 17/12136 606/199 |
| 2007/0073269 A1 | 3/2007 | Becker |
| 2011/0251509 A1* | 10/2011 | Beyhan ............ A61B 17/12136 600/529 |
| 2013/0146051 A1* | 6/2013 | Nolan ................ A61M 16/022 128/202.16 |
| 2013/0184683 A1* | 7/2013 | Chow ................ A61M 3/0295 604/35 |
| 2015/0209558 A1 | 7/2015 | Charlebois et al. |
| 2018/0092150 A1 | 5/2018 | Kalyanaraman et al. |
| 2019/0099572 A1* | 4/2019 | Lenhardt ........... A61M 16/0003 |

OTHER PUBLICATIONS

European Search Report in EP Application No. 21822249.5-1122/4164727, mailed May 28, 2024 (8 pages).

\* cited by examiner

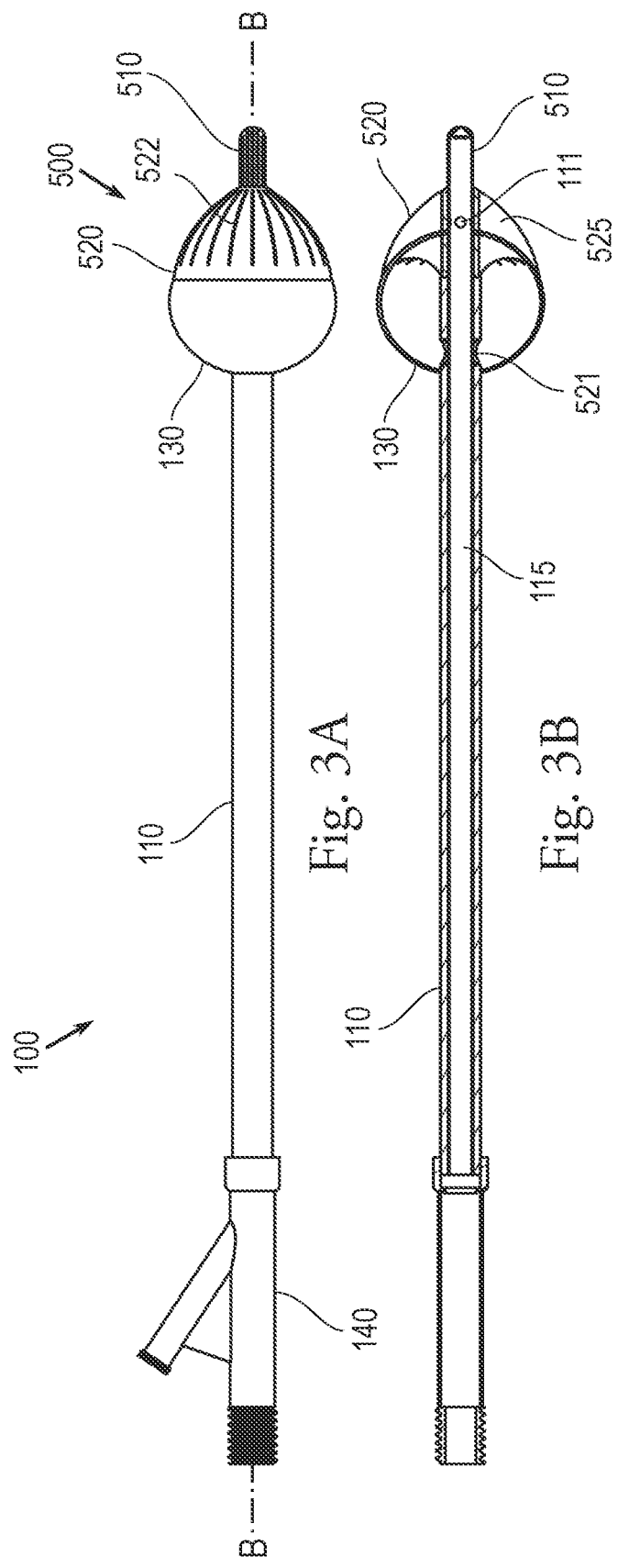

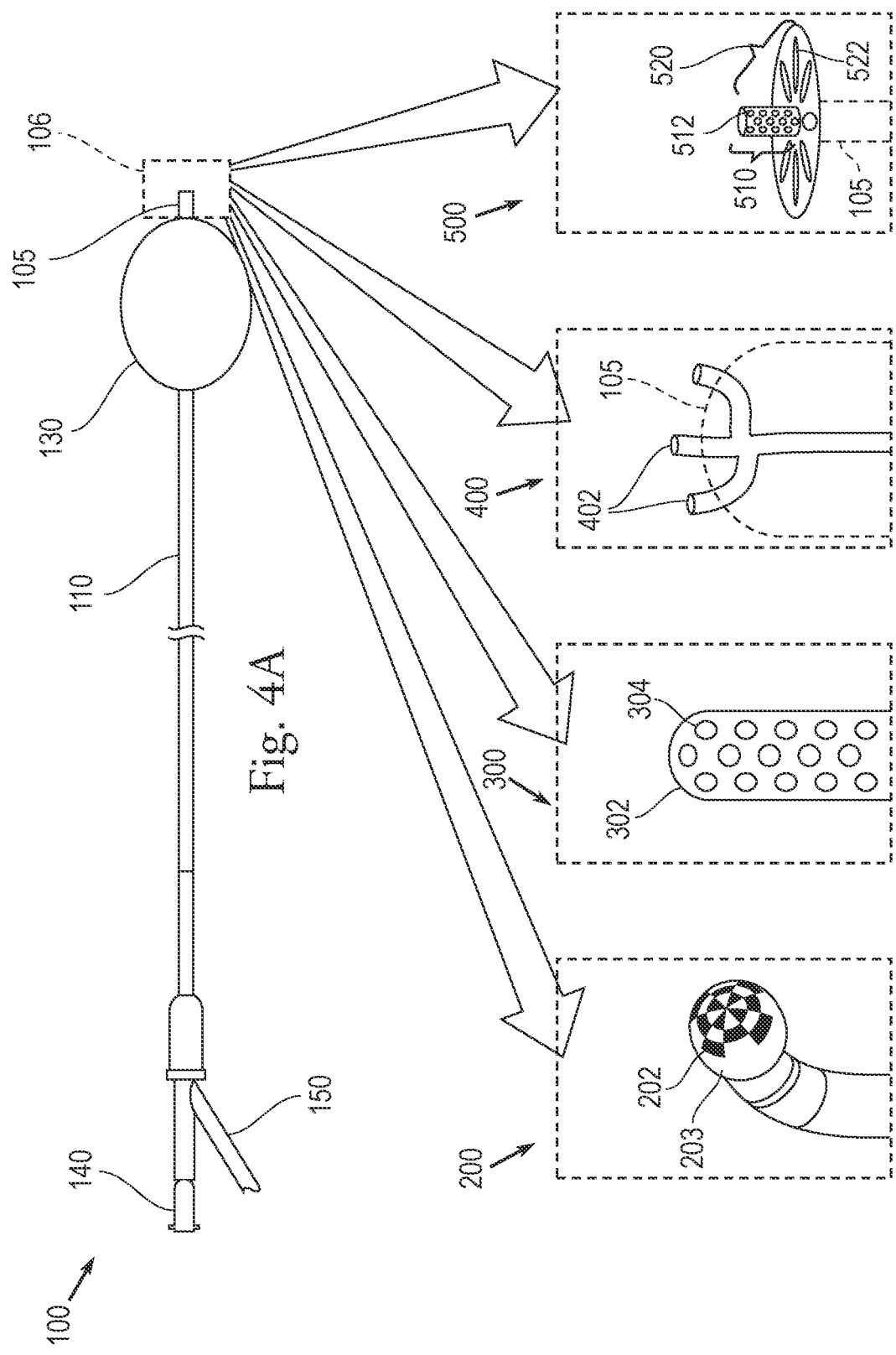

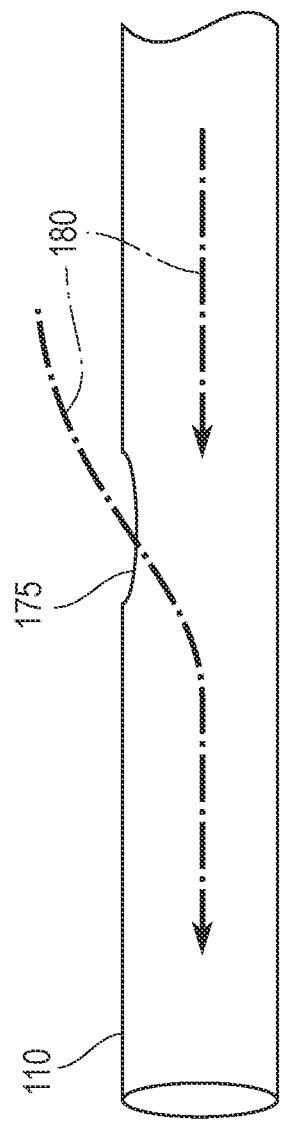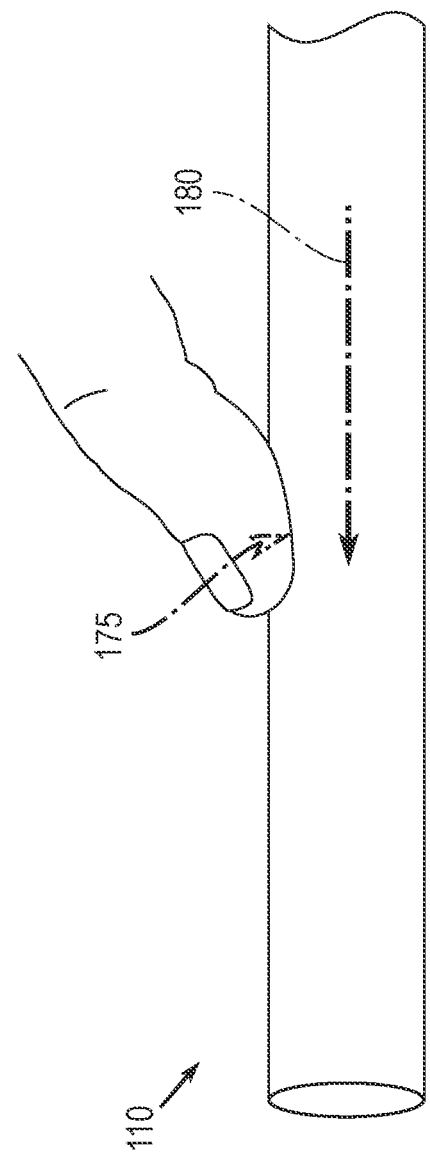
Fig. 5A
Fig. 5B

PHARYNX ASPIRATION DEVICE FOR MINIMIZING INFECTIOUS PARTICLE EXPOSURE DURING ENDONASAL SURGERIES

CROSS-REFERENCE TO RELATED APPLICATIONS

The present application is a U.S. National Phase Application under 35 U.S.C § 371 of International Patent Application No. PCT/US2021/036735, filed Jun. 10, 2021, which claims priority to and the benefit of U.S. patent application Ser. No 63/037,930, file on Jun. 11, 2020, each of which are incorporated by reference herein as if expressly set forth in their respective entirety herein.

TECHNICAL FIELD

The present disclosure is generally directed to medical devices that are used during endonasal surgeries and more particularly, to pharynx aspiration devices configured to minimize the infectious particle exposure during endonasal surgeries.

BACKGROUND

There are many types of surgical procedures with one class being endonasal surgeries. Endonasal surgery comprises an endoscopic endonasal surgery that is a minimally invasive technique that allows a surgeon to go through the nose to operate within the nasal cavity, the sinuses or in the front or bottom of the brain and top of the spinal cord. Endoscopic endonasal surgery is thus a type of surgical procedure to treat problems, such as a tumor, in the front or bottom of the brain or top of the spinal cord. A thin tube called an endoscope is used to let the surgeon do the surgery. Instead of cutting through the skull, a surgeon can put the scope and tiny tools through the nose to reach the target site. This lets the healthcare provider reach areas that are hard to reach in other ways. Recovery is also faster and less painful than with open surgery.

By passing through the nose, the surgeon can access the nasopharynx. The nasopharynx is, by definition, the upper part of the throat behind the nose. It is a part of the pharynx, which comprises three separate segments: the nasopharynx, oropharynx, and the hypopharynx. The nasopharynx is the space above the soft palate at the back of the nose and connects the nose to the mouth, which allows a person to breathe through the nose. The soft palate separates the nasopharynx from the oropharynx, which sits just below the soft palate. The nasopharynx remains open even when surrounding muscles flex so that the person can continue to carry on respiratory functions. The nasopharynx is surrounded by the salpingopharyngeal fold and tubal tonsils, which can become inflamed when infected. It contains adenoid tissue, which fights infection, and the openings to the Eustachian tubes, which lead to the ears. It provides a major drainage path for lymphatic fluids and generally drains into the throat, nose or ears.

Exposure of clinical personnel, even provided appropriate personal protective equipment (PPE), is a major risk during aerosolizing procedures. Ear, nose and throat (ENT) surgical procedures are among the most dangerous for medical professional to perform, as treatment inherently involves the mucosal tissue where viruses, such as COVID-19 particles reside. Instrumentation has shown to significantly aerosolize particles within the nasal cavity that can be dispersed into the surrounding operative area. Due to this concern, during times of widespread illness and pandemics, nearly all non-essential ENT surgeries have been postponed indefinitely.

While COVID-19 represents an acute need for minimizing the surgeon's exposure to aerated mucosal tissue and associated infectious particles. Times of widespread illness and pandemics, such as the ongoing COVID-19 pandemic, can act as a catalyst for more lasting procedural changes to limit exposure to these particles.

There is therefore a need for a device that limits the surgeon's exposure to these harmful, aerosolized virus particles.

SUMMARY

In accordance with one embodiment of the present disclosure, a method for minimizing infectious particle exposure during endonasal surgeries comprises the steps of:
introducing an aspiration device through a mouth of a patient and positioning a distal tip within the nasopharynx space, the aspiration device comprising an elongated balloon catheter having an inflatable balloon located within a distal region thereof and a distal aspiration port that is positioned distal to the balloon; inflating the balloon so that the balloon occupies the nasopharynx space; and aspirating any infectious particles within the nasopharynx space via the distal aspiration port.

In another aspect, the present disclosure sets forth a nasopharynx aspiration device for minimizing infectious particle exposure during endonasal surgeries. The device includes an elongated balloon catheter having an inflatable balloon located within a distal region thereof and a distal aspiration port that is positioned distal to the balloon. The distal aspiration port defines a distal end of the nasopharynx aspiration device.

The distal aspiration port includes a superior aerosol aspirator for aspirating infectious aerosol particles and an inferior liquid/solid aspirator for aspirating liquid and/or solid particles. The superior aerosol aspirator has a tubular structure with a plurality of first openings formed circumferentially along a side wall of the tubular structure and the inferior liquid/solid aspirator comprises an expandable sheath that extends radially beyond the superior aerosol aspirator and includes a plurality of second openings formed therein. The expandable sheath is attached along an inner peripheral edge to the elongated balloon catheter at a location that is proximal to the superior aerosol aspirator so as to position all of the plurality of first openings distal to the inferior liquid/solid aspirator. The expandable sheath is attached along an outer peripheral edge to the balloon. The expandable sheath is expandable under inflation of the balloon resulting in a headspace being defined between the balloon and the expandable sheath. The plurality of second openings are in fluid communication with the headspace for collecting the liquid and/or solid particles.

As described herein, the pharynx aspiration device is configured to protect providers operating within the nasal cavity of patients, particularly, those who may be infected with a highly contagious disease, such as COVID-19.

BRIEF DESCRIPTION OF DRAWING FIGURES

FIG. 3A is a side elevation view thereof;

FIG. 3B is a cross-sectional view taken along the line B-B of FIG. 3A;

FIG. 4A is side elevation view of a nasopharynx aspiration device;

FIG. 4B is a perspective view of an aspiration tip according to a first embodiment for incorporation into the device of FIG. 4A;

FIG. 4C is a perspective view of an aspiration tip according to a second embodiment for incorporation into the device of FIG. 4A;

FIG. 4D is a perspective view of an aspiration tip according to a third embodiment for incorporation into the device of FIG. 4A;

FIG. 4E is a perspective view of an aspiration tip according to a fourth embodiment for incorporation into the device of FIG. 4A;

FIG. 5A is a cross-sectional view of a static air inflow port formed along a catheter body showing a first operating state;

FIG. 5B is a cross-sectional view of the static air inflow port showing a second operating state;

DETAILED DESCRIPTION OF CERTAIN EMBODIMENTS

FIGS. 1-6 illustrate various pharynx aspiration devices 100 for minimizing infectious particle exposure during endonasal surgeries. As described herein, the pharynx aspiration device is configured to protect providers operating within the nasal cavity of patients, particularly, those who may be infected with a contagious disease, such as COVID-19. The pharynx aspiration device 100 described herein benefits from not only positively impacting the current COVID response but serves as a solution for all future ENT surgeries upon the end of the current COVID crisis.

Figure 1:
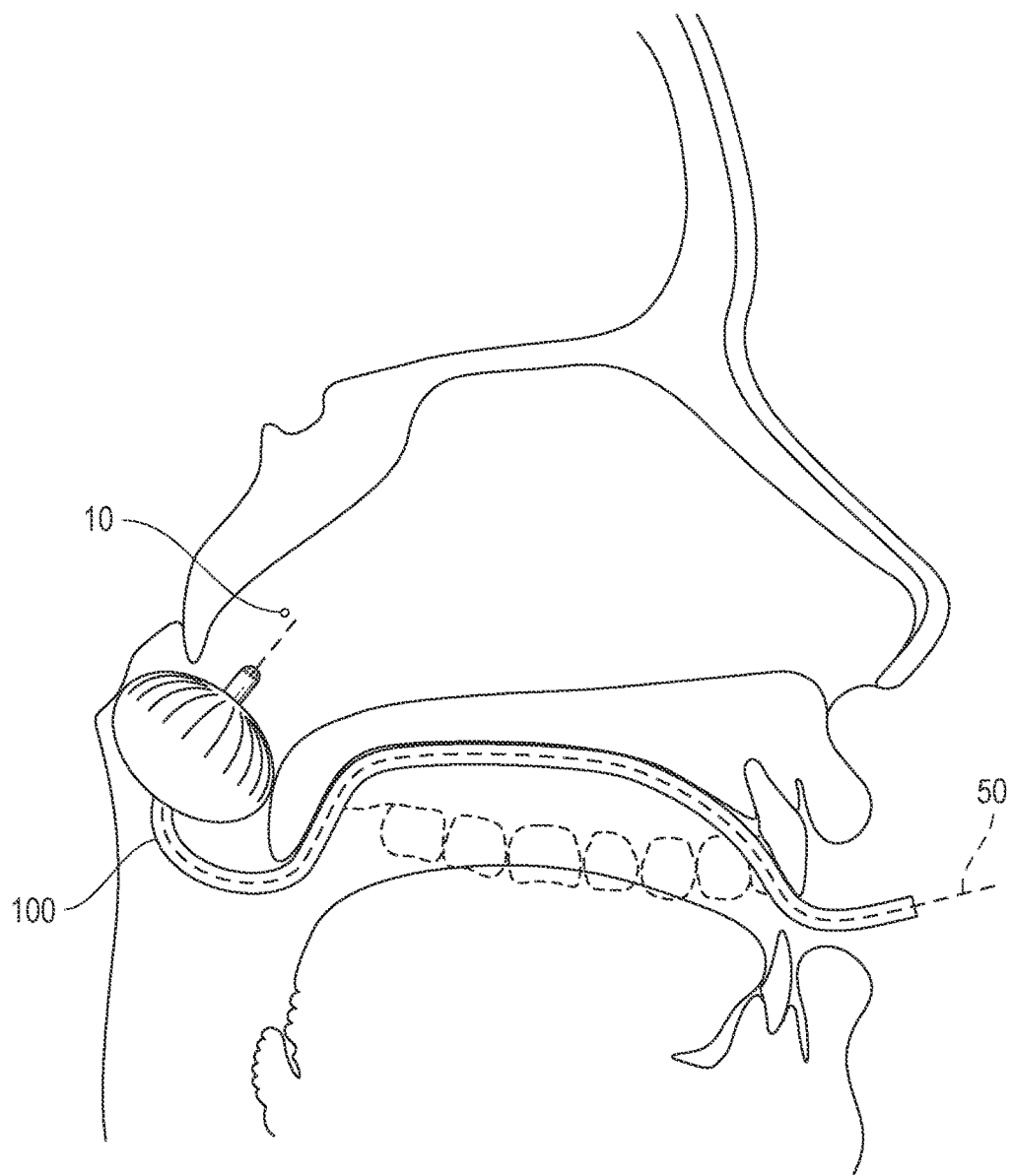
FIG. 1 is a schematic showing the anatomy of the nasopharynx space of a human.
Figure 2:
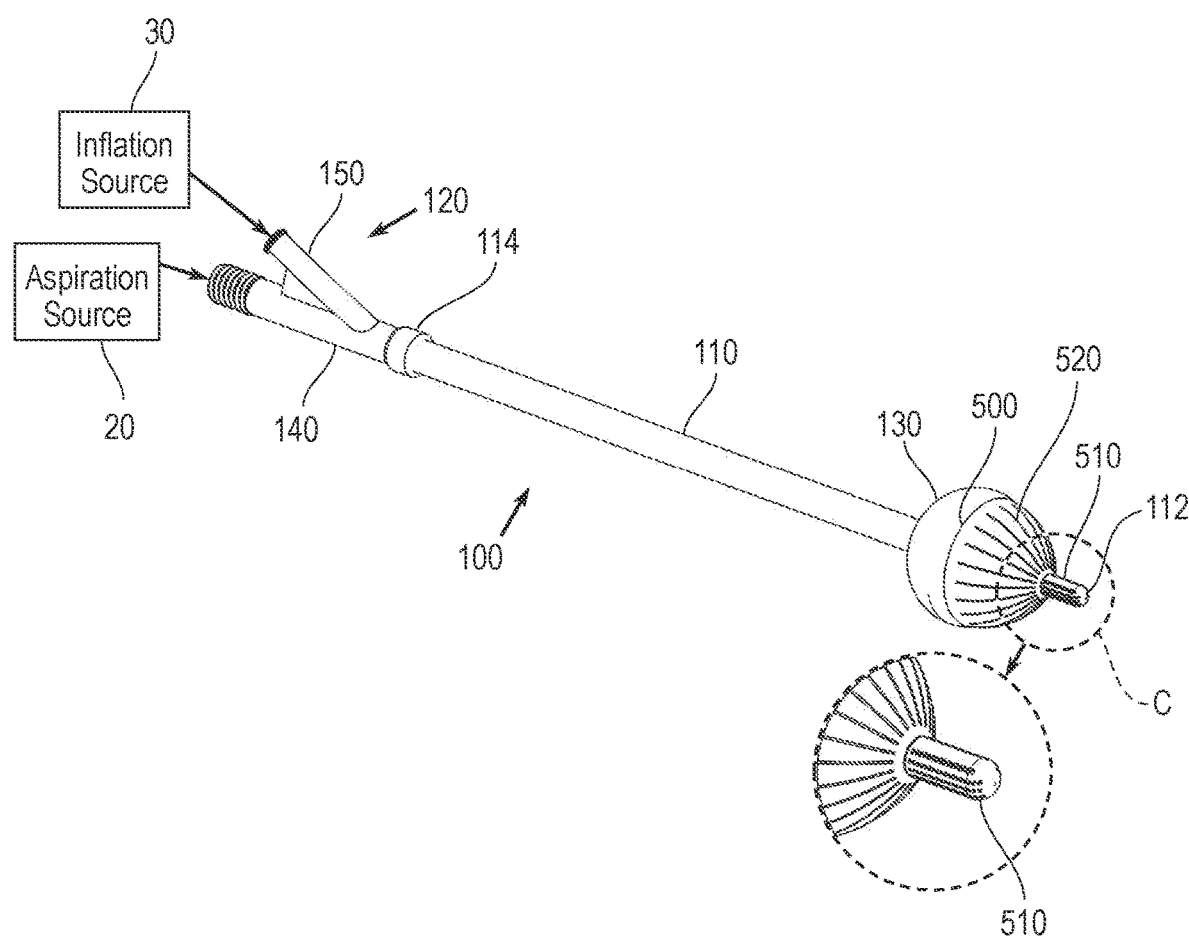
FIG. 2 is a side perspective view of a nasopharynx aspiration device in accordance with one embodiment including an enlargement of the distal tip region.
Figure 6:
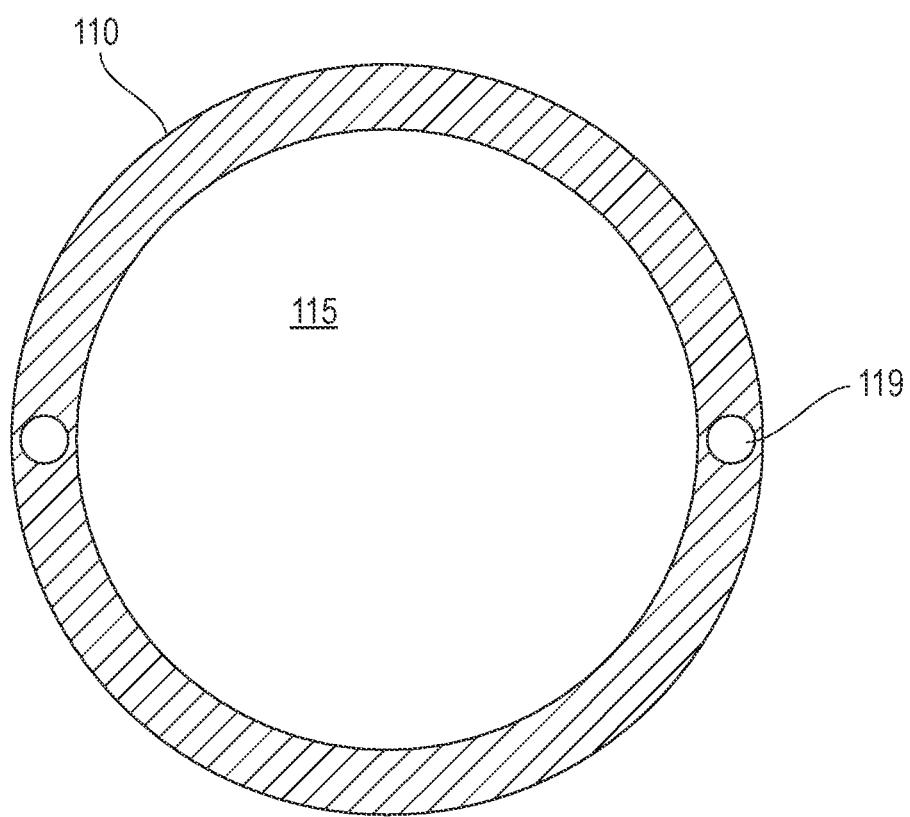
FIG. 6 is a cross-sectional view of a catheter shaft showing a main lumen and secondary lumens.

As shown in FIG. 1 and described in more detail herein, a pharynx aspiration device is particularly suited for insertion into a nasopharynx space 10 or other space of interest of a human or other living being.

The pharynx aspiration device 100 comprises an elongated catheter 110 that has a distal end 112 and an opposite proximal end 114. The distal end 112 can define the distal end of the device 100. The elongated catheter 110 can thus be a hollow, flexible (bendable) tubular structure that is open at both the distal end 112 and the proximal end 114. As shown in FIG. 3B, a first lumen 115 is formed in and extends longitudinally within the catheter 110. The first lumen 115 can be considered to be a center or main lumen.

The elongated catheter 110 is formed of a conventional catheter material that is flexible to allow the catheter 110 to be inserted into the patient's nose and be advanced into the nasopharynx space 10. Thus, some bending is permitted. The catheter 110 also includes an inflatable balloon 130 that is positioned close to but slightly spaced from the distal end 112. The balloon 130 is intended to be inflated for securing and holding the device 100 in place at the target site (e.g., within the nasopharynx space 10). As is known, when the balloon 130 is inflated it contacts surrounding tissue and fills a space (e.g., the nasopharynx space 10) so as to anchor the device 100 in place during the surgical procedure.

The inflatable balloon 130 surrounds the catheter 110 and can take any number of different shapes and can be formed of suitable balloon materials. In the illustrated embodiment, the balloon 130 is spherical shaped or slightly oval shaped; however, other shapes are possible so long as the balloon 130 in its inflated state is wedged within the nasopharynx space 10. The balloon 130 is attached to the catheter 110 in surrounding fashion using conventional techniques.

As described herein, the balloon 130 is inflated by injection of inflation media from an inflation source (FIG. 1) into the balloon 130 to cause expansion thereof around the catheter 110. One conventional inflation media is a saline solution which, as described below, is delivered into the inside of the balloon 130 for inflation thereof and is removed from the inside of the balloon 130 for deflation thereof. As is known, traditional fluid transfer systems, such as pumps, can be used to deliver and remove the inflation media from the balloon 130.

In one embodiment, the balloon 130 is formed of very low durometer urethane or a similar material to allow for space-filling. Balloon 130 can be a non-compliant balloon, semi-compliant, or compliant balloon.

At the proximal end 114 of the catheter 110, there is a port adapter or connector 120. The port adapter 120 is coupled to the proximal end 114 of the catheter 110 and can also take the form of a handle or the like to permit the catheter 110 to be grasped and held. It will be understood that in some embodiments, the port adapter 120 can be integrally formed with the catheter 110. The illustrated adapter 120 has a first port in the form of an aspiration port 140 that is in fluid communication with an aspiration source (aspiration device) 20 and a separate second port in the form of a balloon inflation port 150 that is in fluid communication with the inflation source 30. In one embodiment, the aspiration source 20 can be a vacuum source or the like and the inflation source 30 can be a pump and reservoir. In the illustrated embodiment, the aspiration port 140 is coaxial with the catheter body 110, while the inflation port 150 comprises a leg that extends outwardly (laterally) away from the aspiration port 140. It will be understood that while the port 150 is described as being an inflation port for delivering inflation media for inflating the balloon, this same port is used to deflate the balloon 110 by withdrawing the balloon inflation media from the balloon. The function of these two ports 140, 150 can thus be reversed so long as the internal lumen structure is likewise adapted.

Each of these ports 140, 150 is designed to be sealingly connected to external equipment. For example, the aspiration port 140 is configured to be attached to equipment (e.g., wall suction in the OR) that generates negative pressure for aspirating fluid from the distal end 114 of the catheter 110. The inflation port 150 is connected to the source of inflation media 30 and a pump or the like that either pumps the inflation media into the balloon 130 for inflation thereof or withdraws the inflation media from the balloon 130 for deflation of the balloon 130.

In one embodiment, the length of the catheter 110 from the distal end 112 to the proximal end 114 (i.e., from a distal end of the adapter 120 to the distal end 112) can be between 30 cm and 60 cm. Moreover, the length of the inflated balloon 130 can be between 3 cm and 5 cm. However, these values are only exemplary and not limiting of the scope of the present disclosure.

As is known, the body of the catheter 110 itself can include multiple lumens formed therein. These lumens can take the form of a larger center lumen (i.e., lumen 115) defined by the wall of the catheter 110 and/or can take the form of longitudinal bores (e.g., lumen 119) that are formed directly within the wall of the catheter body (See, FIG. 6). For example, the aspiration port 140 can be in fluid communication with the first lumen 115 (e.g., a center lumen) through which fluid is aspirated from the target site, while the inflation port 150 can be connected to a side lumen 119 (FIG. 6) that is formed in the body of the catheter 110 and is offset from the first (center) lumen 115. At a location along the catheter body that is within the confines of the balloon 130, there can be a hole 521 (e.g., a side opening) (FIG. 3B) through which the inflation media exits the inflation lumen and enters into the inside of the balloon 130 (conversely, to deflate the balloon 130, the inflation media is withdrawn through this hole 521).

It will also be appreciated that the catheter 110 can be of the type that is steerable/controllable in that the user can controllably bend (deflect) the distal tip region of the catheter 110. One skilled in the art would readily understand how to incorporate such features into the catheter 110 and typically, such control features take the form of wires or the like that pass through lumens (e.g., lumen 119) formed in the catheter body and are fixedly attached to the catheter body at select locations. When a select wire is pulled, deflection of the catheter body 110 results.

The open or partially open distal end 112 of the catheter 110 acts a distal aspiration port which is located distal to the balloon 130 and is intended to be placed at the surgical site at which aspiration is desired. The open or partially open distal end 112 is the distal end of the aspiration lumen (e.g., first lumen 115) formed within the catheter 110 and therefore, the negative pressure applied to aspiration port 140 causes any fluid (e.g., blood) and solids (e.g., debris) at the site to be aspirated into and through the first lumen 115 of the catheter 110 and more importantly, results in all static air and aerosolized infectious particles (e.g., virus particles) to be removed via the distal aspiration port at the open distal end 112. As shown, the distal end 112 is located distal to the balloon 130 since the balloon 130 is coupled to and surrounds the catheter body 110.

The distal aspiration port at the open or partially open distal end 112 is thus configured to achieve the above described objectives. The design and construction of this distal aspiration port can be tailored depending upon different parameters; however, in general, the designs ensure that negative pressure is continually maintained (e.g., within the lumen 115) even as blood and other debris is generated and removed.

FIG. 4A illustrates the device 100 including a distal aspiration port region 105 at the distal end. A box 106 surrounds the distal aspiration port region 105 to indicate that this portion of the device 100 can take any number of different constructions as described in more detail below with respect to FIGS. 4B to 4E which illustrate exemplary constructions for the distal aspiration port region 105. All of these illustrated distal aspiration ports are configured to aspirate fluid from the surgical site. The distal aspiration port region 105 can be defined by a rounded tip to prevent injury.

FIG. 4B illustrates a distal aspiration port 200 that is formed at the distal end 112 of the catheter 110 (FIG. 4A). The distal aspiration port 200 can have a rounded (spherical) shaped head 203 and includes a plurality of openings 202 formed along the rounded head 203. The openings 202 are spaced apart from one another and can be formed at the distal tip (distal end of the rounded shaped head 203) itself as well as along the rounded surface that defines the head 203. In this construction, there can be a centermost grouping of openings 202 as well as a series of openings 202 that radially surround the centermost grouping of openings 202. It will be appreciated that all of the openings 202 can have the same shape and size or the openings 202 can have different shapes and sizes. Also, the openings 202 can have an asymmetric arrangement or can be formed in a symmetric arrangement. The spherical nature of the head 203 gives this embodiment a ball-like shape. As shown, there can be a degree of curvature to the distal aspiration port 200 in that the catheter body (catheter 110) can be manipulated so as to bend and curve (e.g., under action of steering wires). It will also be understood that the catheter can also be formed with a prebaked curvature in that during manufacturing, if desired, the curvature can be set into the catheter.

It will be appreciated that all of the openings 202 communicate with the aspiration lumen (first lumen 115) formed in the catheter 110 for aspirating fluid at the target site.

FIG. 4C illustrates an alternative distal aspiration port 300 that is defined by a planar (flat) head 302 (that can have any number of different peripheral shapes) and includes a plurality of openings 304 formed therein. The head 302 can terminate in a rounded end as shown. The tubular catheter transitions to the flat head (like a duck bill). The openings 304 can be uniform in terms of shapes and/or sizes or alternatively, the openings 304 can have different shapes and/or sizes. This type of construction has a swiss cheese like appearance.

This type of distal aspiration port can have a pancake type due to its flat shape. The flat head 302 can be defined by a pair of parallel, flat walls with a hollow space therebetween with openings 304 being formed in one or both of these parallel, flat walls.

It will be appreciated that all of the openings 304 communicate with the aspiration lumen (first lumen 115) formed in the catheter 110.

FIG. 4D illustrates an alternative distal aspiration port 400. The distal aspiration port 400 can be characterized as being a divergent aspiration tip design in which the distal end 112 of the catheter 110 can be a rounded closed tip which includes a plurality of open conduits 402 that can take the form of fingers that are formed separately in the distal tip (region 105) and can extend beyond the distal tip (region 105) as shown in FIG. 4D. It is also possible for at least the portions of the fingers 402 that extend beyond the rounded distal tip (region 105) to be formed of a flexible material, such as an elastomer or rubber, or a semi-rigid material, so as to represent an atraumatic element in that if such finger contacts a structure such as tissue, it will flex and bend. In the illustrated embodiment, there are three fingers 402 that are spaced apart from one another. As with the other embodiments, the fingers 402 fluidly communicate with a common aspiration lumen (lumen 115 connected to aspiration port 140) (FIG. 3B).

In certain embodiment, the fingers 402 are formed of a suitable polymeric material that allows each finger 402 to be readily bent so as to assume a reconfigured position. In other words, the finger 402 can be bent and angled in a desired direction and will maintain this position until the user bends the finger 402 to another position. Alternatively, the fingers 402 can be set at fixed positions and are not manipulated by the user and bent, etc. The fingers 402 can still be flexible and can bend but once the applied force is removed, they will assume their fixed positions.

Each finger 402 thus defines a flow path into the distal tip region 105 and in particular, into the lumen 115 to aspirating fluid through each finger into the lumen 115.

Figure 7:
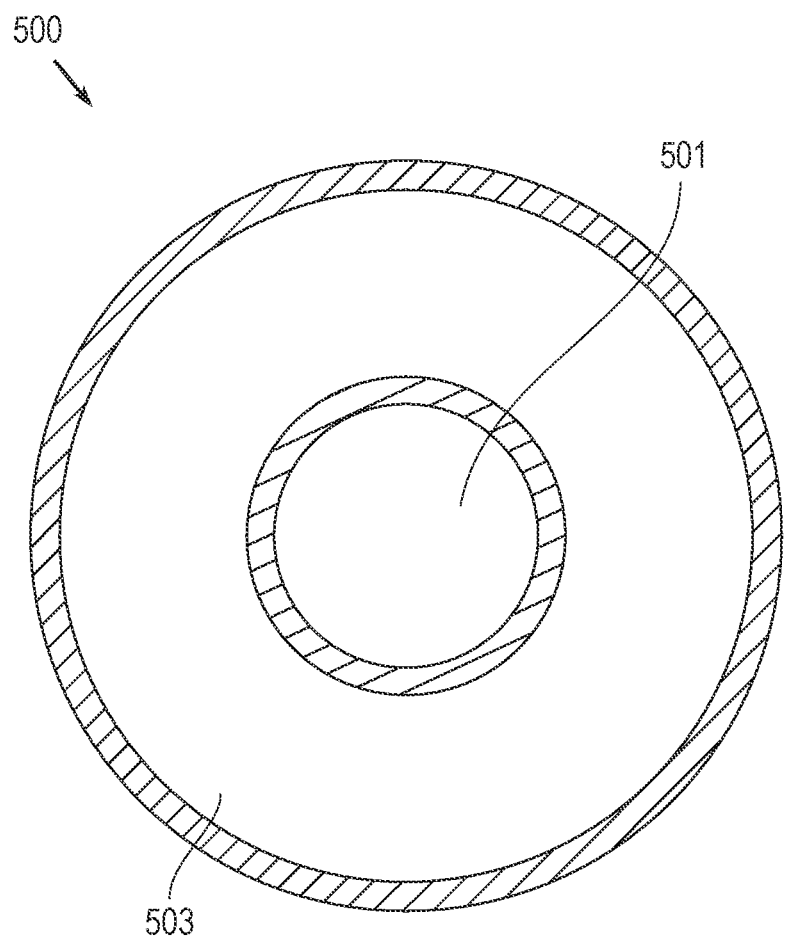
FIG. 7 is a cross-sectional view of a catheter shaft showing two lumens.

FIGS. 3A, 3B, and 4E illustrates another distal aspiration port 500 which is constructed to have several independent aspiration lumens. More specifically, the distal aspiration port 500 can include a separate aerosol aspirator (superior aerosol aspirator) 510 and a separate liquid/solid aspirator (inferior liquid/solid aspirator) 520 that operate via independent lumens formed in the catheter 110. For example, FIG. 7 shows that the superior aerosol aspirator 510 can be in fluid communication with a first lumen 501 and the inferior liquid/solid aspirator 520 can be in communication with a second lumen 503. The aspirator 510 comprises a superior aerosol aspirator that is located distal to the liquid/solid aspirator 520 and represents the distalmost structure of the distal tip of the catheter 110 (FIG. 3A). As shown, the distal aspiration port 500 can be located at the closed rounded distal end of the catheter 110.

As mentioned, the superior aerosol aspirator 510 is configured to aspirate aerosol (virus particles) and can be in the form of a tubular structure that extends axially outward from the distal end and can therefore be considered to be an extension from the body of catheter 110. The diameter of the tubular structure is less than the diameter of the body of the catheter 110. This tubular structure includes a plurality of openings 512 that communicate with the hollow interior (inner lumen) of the tubular structure. As shown, the openings 512 can be formed along the side of the tubular structure. The distal end of the tubular structure can be open or it can be closed so that flow into the inner lumen is only through the side openings 512. The illustrated openings 512 are circular; however, other shapes are possible.

The hollow interior of the tubular structure of the superior aerosol aspirator 510 is in fluid communication with the inner lumen 115 of the body of the catheter 110 and thus, aerosol that flows into the superior aerosol aspirator 510 flows into the aspiration lumen (i.e., the first lumen 115).

The tubular structure can have a cylindrical shape; however other shapes are equally possible.

The liquid/solid aspirator 520 is located proximal to the superior aerosol aspirator 510 and extends radially outward from the superior aerosol aspirator 510 as shown. The liquid/solid aspirator 520 is intended to aspirate liquid, such as blood, as well as solid debris. The liquid/solid aspirator 520 has a structure that includes openings 522 formed therein and being spaced apart from one another. As shown, the structure can be in the form of a tent-like structure that surrounds the superior aerosol aspirator 510. The openings 522 are radially spaced apart and can have elongated shapes and thus can be considered to be elongated slots or slits. As a result, the openings 522 can have different shapes and/or sizes compared to the openings 512 given their different function of aspiration of liquids and solids as opposed to aerosol.

The liquid/solid aspirator 520 can be attached at one end (proximal end) to the balloon 130 itself and is attached at another end (distal end) to the distal end portion of the catheter body 110 (See, FIG. 3B). This attachment point to the catheter body 110 is thus proximal to the superior aerosol aspirator 510. The liquid/solid aspirator 520 covers only the distal end portion of the balloon 130 and as mentioned, defines headspace 525. Headspace 525 can be thought of as being annular shaped.

The liquid/solid aspirator 520 can be considered to be an expandable sheath or sleeve that expands as the balloon inflates and defines an internal headspace 525 (open space) between the liquid/solid aspirator 520 and the balloon/catheter body as shown in FIGS. 3A and 3B. Headspace 525 is formed since one end of the liquid/solid aspirator 520 is fixed, while the other end expands. The material of the liquid/solid aspirator 520 is thus capable of such expansion and then subsequent contraction (i.e., collapses as the balloon deflates). Various polymeric films are suitable.

In other words, as shown in FIGS. 3A and 3B, the liquid/solid aspirator 520 is formed as an expandable sheath or sleeve that partially covers the balloon 130 and is fixedly attached thereto. Since the attachment of the liquid/solid aspirator 520 to the catheter 110 is located distal to the balloon 130, headspace 525 is formed. The expanded liquid/solid aspirator 520 defines a distal facing surface area in which the openings 522 are formed and are open. Since the liquid/solid aspirator 520 is formed of an expandable material, as the liquid/solid aspirator 520 expands, the size of the openings 522 can expand (increase) much like how a hole in a balloon expands when the surrounding balloon is stretched. Insertion of the expanded liquid/solid aspirator 520 into the target space (nasopharynx space 10 (FIG. 1)) thus allows fluid to flow into the openings 522 and into the headspace 525 from which it flows through openings(s) (e.g., opening 521) and enters into the aspiration lumen (e.g., lumen 115). It will be understood that with reference to FIG. 7, the opening 521 can be formed so as to be in fluid communication with one of lumen 501 and lumen 503.

FIGS. 3A and 3B also depict the distal aspiration port 500. There can be a hole 521 in the body of the catheter 110 within this headspace 525 that provides a fluid connection between the liquid/solid aspirator 520 and one lumen, such as the first lumen 115, which comprises the aspiration lumen of the catheter 110. It is through this lumen that the surrounding liquid/solids can be aspirated at the nasopharynx space 10 (FIG. 1). Liquid/solid thus enters through the openings 522 into the headspace 525 and then into the aspiration lumen that is formed in the catheter 110 through which it is aspirated.

The slits 522 are thus preferably formed in areas of the liquid/solid aspirator 520 that are distal to the proximal attachment region of the liquid/solid aspirator 520 that is defined as the area at which the liquid/solid aspirator 520 attaches to the balloon 130. By forming them in this location, the full length of the openings 522 are open when the balloon 130 is inflated thus allowing fluid/solid flow through the openings 522 into the headspace 525.

FIG. 4E shows the liquid/solid aspirator 520 prior to attachment of its proximal end to the balloon 130 which is not shown in FIG. 4E. The peripheral edge of the liquid/solid aspirator 520 is attached to the balloon 130 using conventional techniques, such as bonding techniques, etc. The shape of the liquid/solid aspirator 520 complements the shape of the balloon 130 and therefore, as shown, prior to expansion, the liquid/solid aspirator 520 can have a circular shape and the openings 522 appears like spokes formed around a hub which in this case is the superior aerosol aspirator 510.

The device 100 can also be configured to allow for varying the aspiration level. As shown in FIGS. 5A and 5B, the catheter 110 can include a static air inflow port 175 formed in the catheter body. The static air inflow port 175 can thus be formed in the side wall of the catheter body and communicates directly with the aspiration port (lumen) formed in the catheter body. The static air inflow port 175 is designed to be a thumb hole port in that the user can place his or her thumb over the static air inflow port 175 to obstruct airflow into the aspiration lumen.

FIG. 5A illustrates a first operating mode which comprises a minimal intranasal air suction mode. In this first operating mode, the static air inflow port 175 is completely open which allows for atmospheric air to flow into aspiration lumen, thereby reducing the strength of the suction (negative pressure). Air flow is indicated by arrow 180. Conversely, FIG. 5B illustrates a second operating mode which comprises a maximum intranasal air suction mode. In this second operating mode, the user completely covers the static air inflow port 175 with a thumb. With no atmospheric air bleeding into the system (into the aspiration lumen 115), the suction strength is maximized (as indicated by arrow 180).

Additional design components include a placement tool for accurate placement of the device 100 via the oral cavity. The placement tool can then be removed for the remainder of the operation. The balloon is also able to be rapidly deflated and removed in case of a medical need for rapid access through the oral cavity. The aspiration device 100 allows for the injection of saline against the normal airflow to ensure clogs can be displaced and aspiration can be maintained. Suitable placement tools include but are not limited to a semi-rigid guidewire 50 (FIG. 1) to place the device using the Seldinger technique. In addition, it is known for balloons of balloon catheters to include detachable markings, such as radiopaque markings formed on the balloon to allow for imaging and detection of the location of the balloon catheter.

Once the endonasal surgery is complete, the aspiration device 100 is removed from the nasopharynx space and then ultimately removed through the mouth.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt an instrument, situation or material to the teachings of the invention without departing from the essential scope thereof. Therefore, it is intended that the invention not be limited to the embodiment disclosed as the best mode contemplated for carrying out this invention, but that the invention will include all embodiments falling within the scope of the appended claims.

What is claimed is:

1. A nasopharynx aspiration device for minimizing infectious particle exposure during endonasal surgeries comprising: an elongated balloon catheter having an inflatable balloon located within a distal region thereof and a distal aspiration port that is positioned distal to the balloon, the distal aspiration port defining a distal end of the nasopharynx aspiration device, wherein the distal aspiration port includes a superior aerosol aspirator for aspirating infectious aerosol particles and an inferior liquid/solid aspirator for aspirating liquid and/or solid particles, wherein the superior aerosol aspirator comprises a tubular structure with a plurality of first openings formed circumferentially along a side wall of the tubular structure and the inferior liquid/solid aspirator comprises an expandable sheath that extends radially beyond the superior aerosol aspirator and includes a plurality of second openings formed therein, the expandable sheath being attached at a distal end to the elongated balloon catheter at a location that is proximal to the superior aerosol aspirator so as to position all of the plurality of first openings distal to the inferior liquid/solid aspirator, the expandable sheath being attached at a proximal end to the balloon, the expandable sheath being expandable under inflation of the balloon resulting in a headspace being defined between the balloon and the expandable sheath, the plurality of second openings being in fluid communication with the headspace for collecting the liquid and/or solid particles.

2. The nasopharynx aspiration device of claim 1, wherein the expandable sheath covers less than 50% of a surface area of the balloon.

3. The nasopharynx aspiration device of claim 1, wherein the plurality of first openings and the plurality of second openings are in fluid communication with a common aspiration lumen.

4. The nasopharynx aspiration device of claim 1, wherein the plurality of first openings are in fluid communication with a first aspiration lumen and the plurality of second openings are in fluid communication with a second aspiration lumen that is independent and separate from the first aspiration lumen.

5. The nasopharynx aspiration device of claim 1, wherein at least a portion of the distal aspiration port is located distal to a distal end of the elongated balloon catheter.

6. The nasopharynx aspiration device of claim 1, wherein the elongated balloon catheter has one or more holes that are in fluid communication with the headspace and provide an entrance into an aspiration lumen formed in the elongated balloon catheter.

7. The nasopharynx aspiration device of claim 6, wherein the one or more holes are formed through the elongated balloon catheter at a location between a distal end of the balloon and the distal end of the expandable sheath.

8. The nasopharynx aspiration device of claim 1, wherein the balloon and the expandable sheath are formed of an elastomeric polymer.

9. The nasopharynx aspiration device of claim 1, wherein the tubular structure has a diameter that is less than a diameter of the elongated balloon catheter.

10. The nasopharynx aspiration device of claim 1, wherein each of the plurality of second openings comprises an elongated slot formed in the expandable sheath that extend radially outward from the distal end of the expandable sheath toward the proximal end of the expandable sheath.

11. The nasopharynx aspiration device of claim 1, wherein the plurality of second openings are formed circumferentially within the expandable sheath.

12. The nasopharynx aspiration device of claim 1, wherein the headspace has an annular shape.

13. The nasopharynx aspiration device of claim 1, wherein each second opening of the plurality of second openings is defined by a first area in a relaxed state of the expandable sheath and is defined by a greater second area in an expanded state of the expandable sheath.

* * * * *